United States Patent [19]

Poindexter

[11] Patent Number: 4,505,859

[45] Date of Patent: Mar. 19, 1985

[54] PREPARATION OF 2-HALOETHYLAMIDES

[75] Inventor: Graham S. Poindexter, Evansville, Ind.

[73] Assignee: The Dow Chemical Company, Midland, Mich.

[21] Appl. No.: 309,961

[22] Filed: Oct. 9, 1981

[51] Int. Cl.$^3$ .................. C07C 118/00; C07C 102/00
[52] U.S. Cl. .................. 260/453 P; 548/229; 260/455 A; 260/959; 560/30; 560/161; 564/55; 564/90; 564/95; 564/98; 564/106; 564/156; 564/183; 564/209
[58] Field of Search .................. 564/183, 209, 156, 98, 564/90, 96; 548/229; 260/453 P, 455 A, 959; 560/30, 161

[56] References Cited

U.S. PATENT DOCUMENTS

| 2,303,177 | 11/1942 | Schlack | 260/239 |
|---|---|---|---|
| 2,399,118 | 4/1946 | Homeyer | 548/229 |
| 2,617,825 | 11/1952 | Wood | 564/386 |
| 3,052,669 | 9/1962 | Gavlin et al. | 260/239 E |
| 3,108,115 | 10/1963 | Little et al. | 260/239 E X |
| 3,133,932 | 5/1964 | Horn et al. | 260/239 E X |
| 3,152,147 | 10/1964 | Vargha et al. | 260/239 E X |
| 3,193,559 | 7/1965 | Regnier et al. | 548/229 X |
| 3,221,021 | 11/1965 | Hickner | 548/229 X |
| 3,404,172 | 10/1968 | Tomalia | 260/239 E X |
| 3,449,396 | 6/1969 | Tomalia | 260/239 E X |
| 4,097,262 | 6/1978 | Cheng | 548/229 X |
| 4,416,818 | 11/1983 | Poindexter | 548/531 X |

OTHER PUBLICATIONS

Mundy et al., J. Heterocyclic Chem., 19, (1982), pp. 1221-1222.
C.A., 80, (1974), 59459m, Tanaka et al.
Degering, "An Outline of Organic Nitrogen Compounds", 1945, Univ. Lithoprinters, Ypsilanti, Michigan, pp. 397, 398 and 415.
Oda et al., B.C.S., Japan, (1962), 35, pp. 1910-1914 and 1915-1920.
Oda et al., C.A. 59, (1963), 3909h.
Herbert Bestian, Justus Liebigs Ann Chem. 566, 210-244, (1950).
Artur Seher, Justus Liebigs Ann Chem. 575, 153-161, (1952).
W. Marckwald et al., Berichte, 34, 3544-3558, (1901).

Primary Examiner—Joseph Paul Brust
Attorney, Agent, or Firm—Douglas N. Deline

[57] ABSTRACT

2-Haloethylamides are prepared by reaction of 2-oxazolidinone or $C_{1-6}$ alkyl or phenyl derivatives thereof with an acid halide.

5 Claims, No Drawings

PREPARATION OF 2-HALOETHYLAMIDES

BACKGROUND OF THE INVENTION

This invention relates to a novel process for preparing 2-haloethylamides by the reaction of 2-oxazolidinone and an appropriate acid halide.

The 2-haloethylamides prepared according to the invention are useful chemical intermediates for preparation of herbicides and other biologically active compounds and photographic products. It is previously known to prepare the 2-haloethylamides by the reaction of ethyleneimine with suitable acid halides. Examples include the reaction of simple carboxylic acid chlorides, A. H. Bestian, *Justus Liebigs Ann. Chem.*, 566, 210 (1950); chloroformates, A. Seeger, *Justus Liebigs Ann. Chem.*, 575, 153 (1962); and sulfonyl chlorides, C. W. Marckwald et al., *Ber.*, 34, 3544 (1901). Generally, excess acid halide is required in order to minimize polymerization, e.g., polyaminoethylation reactions. Additionally, the toxicity of ethyleneimine reduces the utility of these prior art processes. An alternative route to these useful chemical intermediates would therefore be desirable.

SUMMARY OF THE INVENTION

A novel process has now been found for the preparation of haloalkylamides represented by the formula $XCH_2CR_2N(R)_nR'$ where:

X is chloro, bromo or iodo;
R is hydrogen, $C_{1-6}$ alkyl or phenyl;
n is zero or one; and when n is one, R' is selected from the group consisting of R''C(O)—, R'''SO$_2$—, R'''S(O)—, R'''S—, $(C_6H_5)_2NC(O)$—, N≡C—, $(R'''O)_2P(O)$— and

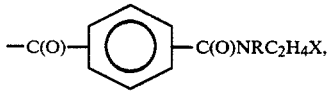

where R'' is alkyl, haloalkyl, aryl, aralkyl, aryloxy or arylthio of up to 20 carbons; and R''' is $C_{1-6}$ alkyl, haloalkyl or phenyl; and when n is zero, R' is O=C= or O=S=.

The process comprises reacting a 2-oxazolidinone or a $C_{1-6}$ alkyl or phenyl derivative thereof of the formula

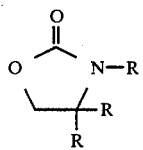

where R is as previously defined with the appropriate acid halide thereby generating carbon dioxide and the desired 2-haloethylamide.

DETAILED DESCRIPTION OF THE INVENTION

One reactant of the invented process is the well-known 2-oxazolidinone or $C_{1-6}$ alkyl or phenyl derivatives thereof. The second reactant is the acid halide corresponding to the remnant desired in the 2-haloethylamide product. By halide is meant chloride, bromide, or iodide. Suitable acid halide reactants include compounds of the formula:

R''C(O)X, R'''SO$_2$X, R'''S(O)X, R'''SX, $(C_6H_5)_2NC(O)X$,

N≡CX, $(R'''O)_2P(O)X$, 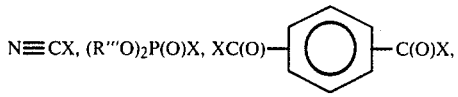

$C(O)X_2$ and $S(O)X_2$ where R'', R''' and X are as previously defined. Preferred are the acid chlorides of the above formula.

The reaction proceeds well with or without solvents at elevated temperatures depending on the relative reactivity of the reactants employed. The course of the reaction is easily monitored by the evolution of carbon dioxide gas.

The reactants are combined in about an equal molar ratio although a greater than stoichiometric amount of one or the other reactant may be employed if desired. Suitable temperatures are from about 80° C. to about 200° C., preferably from about 135° C. to about 160° C.

Suitable solvents, if such are employed, include benzene, toluene and other alkylated benzenes, halogenated benzenes, and dialkylethers of glycols and polyalkylene glycols.

Elevated pressure may be employed if desired, but suitable reaction rates are obtained without using superatmospheric pressure. The preferred operating pressure is about 1 atmosphere. Reaction time ordinarily are from about ½ to 24 hours.

The product is easily recovered from the reaction mixture by ordinary techniques such as extraction with a solvent or crystallization. Purification if desired, may be accomplished by recrystallization.

The by-products formed include carbon dioxide and in the case of the use of phosgene, thionylchloride and other acid dihalides, the corresponding hydrogen-, alkyl-, or phenyl halide depending on the moiety originally attached to the nitrogen of the N-substituted 2-oxazolidinone.

SPECIFIC EMBODIMENTS

Having described my invention, the following examples are provided as illustrative of the invention and are not to be construed as limiting.

EXAMPLE 1

Preparation of N-(2-chloroethyl)benzamide

A mixture of 2-oxazolidinone (8.7 g, 0.10 mole) and benzoyl chloride (14.8 g, 0.10 mole) was placed into a flask equipped with a magnetic stirring bar and a gas evolution tube which was connected to a mineral oil bubbler. The stirred reaction mixture was heated to 135° C. in an oil bath, during which time dissolution of solid and gas evolution occurred. After approximately 30 minutes, all the gas evolution had ceased, as judged by the mineral oil bubbling apparatus. The oil bath was removed and the reaction solution was allowed to cool to ambient temperatures where solidification to a white solid took place. The crude product (mp 92° C.-94° C.), as analyzed by $^1$H NMR spectroscopy, was found to be an 83:17 mixture of the title compound and N-benzoyl-2-oxazolidinone. Recrystallization from methyl ethyl ketone afforded an analytically pure sample: mp 102° C.-104° C.

EXAMPLES 2-5

The compounds listed below were also prepared using the general procedure described in Example 1.

N-(2-chloroethyl)trichloroacetamide by the reaction of 2-oxazolidinone and trichloroacetyl chloride at 80° C.

N-(2-chloroethyl)chloroacetamide by the reaction of 2-oxazolidinone and 2-chloroacetyl chloride at 108° C.

bis-N,N'-(2-chloroethyl)terephthalamide by the reaction of 2-oxazolidinone with terephthaloyl chloride at 160° C.

Phenyl N-(2-chloroethyl)carbamate by the reaction of 2-oxazolidinone with phenyl chloroformate at 135° C.

2,2,2-Trichloroethyl N-(2-chloroethyl)carbamate by the reaction of 2-oxazolidinone and 2,2,2-trichloroethyl chloroformate at 135° C.

Thiophenyl N-(2-chloroethyl)carbamate by the reaction of 2-oxazolidinone with thiophenyl chloroformate at 150° C.

N-(2-choroethyl)methanesulfonamide by the reaction of 2-oxazolidinone with methanesulfonyl chloride at 135° C.

N-(2-chloroethyl)benzenesulfonamide by the reaction of 2-oxazolidinone with benzenesulfonyl chloride at 160° C.

N-(2-chloroethyl)trichloromethylsulfenamide by reaction of 2-oxazolidinone with trichloromethylsulfenyl chloride at 135° C.

N-(2-chloroethyl)diethylphosphonamide by the reaction of 2-oxazolidinone with diethyl chlorophosphate at 135° C.

2-Chloroethyl isocyanate by the reaction of 2-oxazolidinone and phosgene in a mixture of toluene and N,N-dimethylformamide (50:50) at 90° C.

2-Chloroethyl sulfinylamine by reaction of 2-oxazolidinone with thionyl chloride in toluene at 95° C.

Phenyl N-(2-chloroethyl)-N-methylcarbamate by the reaction of N-methyl-2-oxazolidinone and phenyl chloroformate at 145° C.

Phenyl N-(2-chloroethyl)-N-phenylcarbamate by the reaction of N-phenyl-2-oxazolidinone with phenyl chloroformate at 190° C.

What is claimed is:

1. A process for preparing haloalkylamides of the formula $XCH_2CR_2N(R)_nR'$ where:

X is chloro, bromo or iodo;

R is hydrogen, $C_{1-6}$ alkyl or phenyl;

n is zero or one; and when n is one, R' is selected from the group consisting of R''C(O)—, R'''SO$_2$—, R'''S(O)—, R'''S—, $(C_6H_5)_2NC(O)$—, N≡C—, $(R'''O)_2P(O)$— and

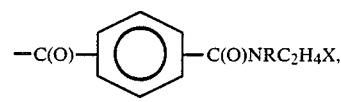

where R'' is alkyl, haloalkyl, aryl, aralkyl, aryloxy or arylthio of up to 20 carbons; and R''' is $C_{1-6}$ alkyl, haloalkyl or phenyl; and when n is zero, R' is O═C═ or O═S═, comprising reacting 2-oxazolidinone or a $C_{1-6}$ alkyl or phenyl derivative thereof of the formula

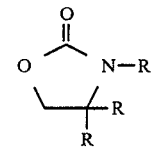

where R is as previously defined, with an acid halide of the formula:

R''C(O)X, R'''SO$_2$X, R'''S(O)X, R'''SX, $(C_6H_5)_2NC(O)X$,

N≡CX, $(R'''O)_2P(O)X$, 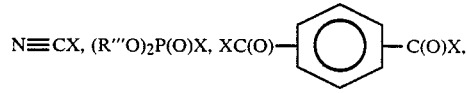

C(O)X$_2$ or S(O)X$_2$ where R'', R''' and X are as previously defined at an elevated temperature, so as to prepare the haloalkylamide.

2. The process according to claim 1 wherein the reaction is conducted at a temperature from about 80° C. to about 200° C.

3. The process according to claim 1 wherein the temperature is from about 135° C. to about 160° C.

4. The process according to claim 1 wherein the acid halide is an acid chloride.

5. The process according to claim 4 wherein the haloalkylamide is selected from the group consisting of N-(2-chloroethyl)benzamide, N-(2-chloroethyl)trichloroacetamide, N-(2-chloroethyl)chloroacetamide, bis-N,N'-(2-chloroethyl)terephthalamide, phenyl N-(2-chloroethyl)carbamate, 2,2,2-trichloroethyl N-(2-chloroethyl)carbamate, thiophenyl N-(2-chloroethyl)carbamate, N-(2-chloroethyl)methanesulfonamide, N-(2-chloroethyl)benzenesulfonamide, N-(2-chloroethyl)trichloromethylsulfenamide, N-(2-chloroethyl)diethylphosphonamide, 2-chloroethyl isocyanate, 2-chloroethyl sulfinylamine, phenyl N-(2-chloroethyl)-N-methylcarbamate and phenyl N-(2-chloroethyl-N-phenylcarbamate.

* * * * *